United States Patent [19]

Strauss

[11] Patent Number: 4,720,922

[45] Date of Patent: Jan. 26, 1988

[54] ANTI-COLLISION DEVICE FOR THE SENSING HEAD OF A MEASURING MACHINE

[75] Inventor: Bernhard Strauss, Nattheim, Fed. Rep. of Germany

[73] Assignee: Carl-Zeiss-Stiftung, Heidenhim/Brenz, Oberkochen, Fed. Rep. of Germany

[21] Appl. No.: 905,111

[22] Filed: Sep. 9, 1986

[30] Foreign Application Priority Data

Sep. 10, 1985 [DE] Fed. Rep. of Germany ....... 3532184

[51] Int. Cl.⁴ .................................................. G01B 7/28
[52] U.S. Cl. .................................... 33/559; 33/172 E; 33/169 R; 33/561
[58] Field of Search ............... 33/1 M, 23.11, 559, 33/560, 561, 556, 558, 503, 504, 572, 169 R, 169 C, 172 E

[56] References Cited

U.S. PATENT DOCUMENTS 4,542,590 9/1985 Cusack ............................. 33/169 R
4,578,873 4/1986 Klingler ........................... 33/556 X

FOREIGN PATENT DOCUMENTS 2083224 3/1980 United Kingdom ............ 33/169 R

*Primary Examiner*—Harry N. Haroian
*Attorney, Agent, or Firm*—Hopgood, Calimafde, Kalil, Blaustein & Judlowe

[57] ABSTRACT

The sensing head of a measuring machine is pendulously suspended via self-centering ball-and-socket structure which affords resilient dislocating relief from its normal precisely centered position of measurement. The resilient connection permits feeedom for such dislocation for all possible directions in spaces, while effectively anchoring the head against torsional deflection about the vertical axis. Once the collision condition is removed, the self-centering suspension assures resumed precision of the at-rest condition in which measurements can be made.

10 Claims, 6 Drawing Figures

ANTI-COLLISION DEVICE FOR THE SENSING HEAD OF A MEASURING MACHINE

BACKGROUND OF THE INVENTION

The sensing head of a measuring machine is that part of the machine that contains the work-contacting probe pin, the latter being deflectable in the sensing process; the sensing head also includes a support which reproduces the at-rest position of said sensing pin with a high degree of precision, as well as (a) the measuring systems for the detection and/or measurement of the deflection of the probe pin, and (b) a number of other precision parts which are necessary for operation. It is therefore desirable to protect the sensing head, which is mounted in an exposed position on the measurement arm of the machine, against collision, such as collision with a workpiece which is to be measured. However, it is not easy to provide such protection since contact between the probe pin and the workpiece must, after all, be permitted.

Therefore, as a rule, one merely protects the most sensitive part of the sensing head, namely, the probe pin, from such excessive forces such as may occur in the event of a collision.

Thus, it is known from West German U No. 7,400,071 to fasten the probe pin to the sensing head by means of permanent magnets. Upon a collision, the probe pin drops off and must then be reassembled to the sensing head by hand. This solution is unsatisfactory since it does not even provide sufficient protection for the probe pin itself, which could be damaged by falling off.

West German A No. 1,909,436, describes a protection device for a copying probe. In that case, the sensor housing itself is pulled elastically by a tension spring against detent elements in the form of a three-point support; the sensor housing can therefore yield in the event of a collision. This known device has the disadvantage that the force of the spring which preloads the sensor housing acts perpendicular to the weight of the sensor housing. If a dependable, well-centered seating of the sensor housing is to be obtained, additional means would therefore have to be provided in order to support the sensor housing, or the spring must have a relatively high tensile force. However, such a requirement is inconsistent with the need for easy yieldability in the event of a collision. Furthermore, the sensor returns automatically into the three-point support used only in the case of relatively small deflections. If larger deflections occur, as can happen, for instance, in the event of a collision upon a fast traverse of the machine, the sensor housing would have to be returned manually into its at-rest position.

BRIEF STATEMENT OF THE INVENTION

The object of the present invention is so to develop a yieldable mounting for an anti-collision device for the sensor head of a measuring machine that the holding force necessary for sufficiently good centering of the operating (at-rest) position of the sensing head is as small as possible and that, after a collision, dependable return into the operating position is assured even in the case of a large collision deflection.

The invention achieves this object by providing a sensing-head mount which consists of a centering member with a large free stroke, the sensing head being disengageably and gravitationally suspended from said member, the mount further comprising a flexible play-free anchoring element which secures the sensing head against torsion.

The sensing head centers itself under its own weight within the centering member, which is preferably a sphere or a spherical segment received in a conical concavity. There is therefore no need for additional biasing, neither is there need for separately supporting any of the weight of the sensing head. The central centering member permits relatively large movements of disengagement and assures the reproducibility of the operating (at-rest) position of the sensing head.

The invention assures protection of the sensing head against collision, in five directions in space. And in the event of need to assure protection against collision in the remaining sixth direction in space, it is advisable to arrange the centering member on a rocker which is biased against the housing and is yieldable in downward direction, should the bias force be exceeded.

It is also advantageous to provide a switch which responds upon disengagement of the centering member, reports the collision and makes it possible to disconnect the drive of the machine.

Furthermore, means can be provided by which the sensing head can be locked in the centering member, should a rigid connection between sensing head and measuring machine be required for certain measurement tasks.

DETAILED DESCRIPTION

The invention will be described in detail in conjunction with the accompanying drawings, in which.

Figure 1:
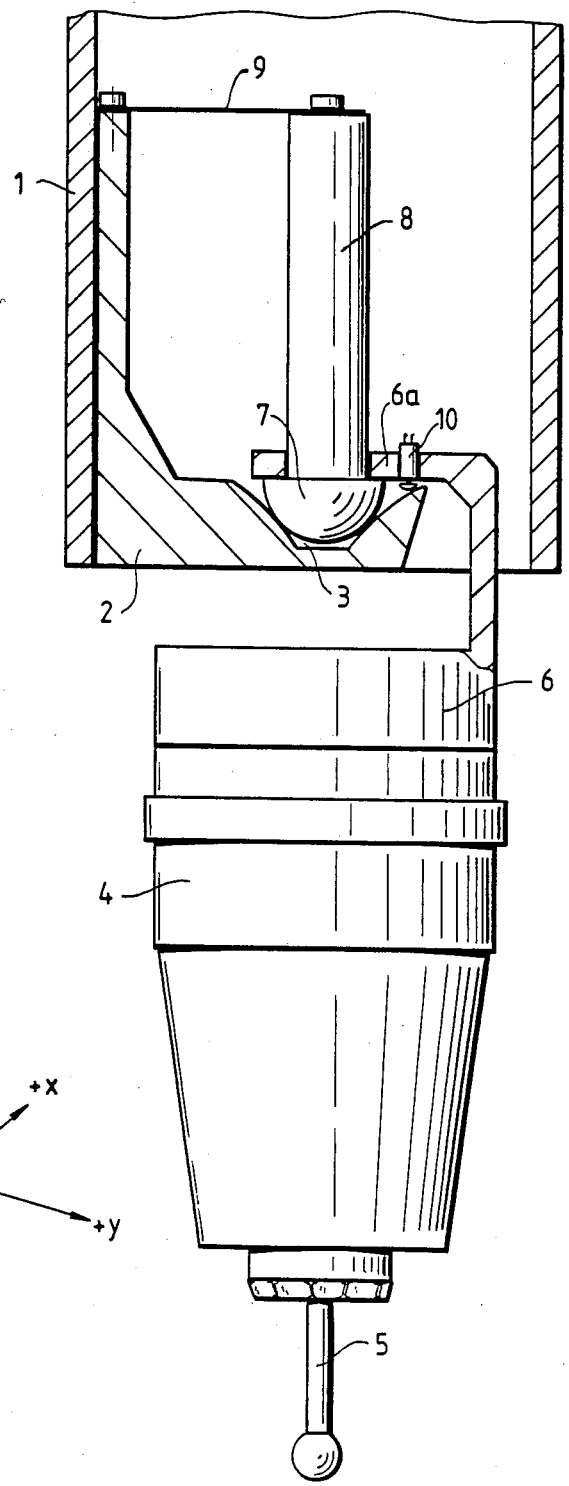
FIG. 1 is a view in elevation, partly broken away and in longitudinal section, for a first embodiment.

In FIG. 1, the vertically displaceable spindle 1 of a coordinate measuring machine, illustratively of portal construction, carries a sensing or probe head 4 with a probe pin 5 movably mounted therein. The sensing head 4 may, for example, be a so-called measurement sensing head, as described in West German C- No. 2,242,355.

The sensing head 4 is suspended from spindle 1 by way of a carrier 6 which is secured to the upper end of head 4. The upper part 6a of carrier 6 is hook-shaped and mounts a hemisphere 7 which is approximately concentric to the longitudinal axis (z) of the sensing head 4. The hemisphere 7 of carrier 6 is suspended in a conical depression 3 in the horizontal part of an L-shaped holding plate or bracket 2 secured within and to spindle 1. The hemisphere 7 and the conical depression 3 from the centering member of the suspension.

Above hemisphere 7, a vertically directed rod 8 is rigidly secured to the carrier 6. The upper end of rod 8 lies in the same plane as the top of the L-shaped bracket 2 mounted to spindle 1. A leaf spring 9 lies in said plane and connects the bracket 2 to rod 8. The leaf spring 9 is flexible about the x and y axes, which be in the horizontal plane but forms a rigid connection against torsion about the vertical axis z. The upper end of rod 8 is therefore secured against displacement in the horizontal plane, i.e., against torsion about the z axis, as well as against translation in the x or y direction. The at-rest position of the sensing head 4 is therefore clearly defined when hemisphere 7 is engaged within the centering depression 3, under the weight of the sensing head.

Figure 3:
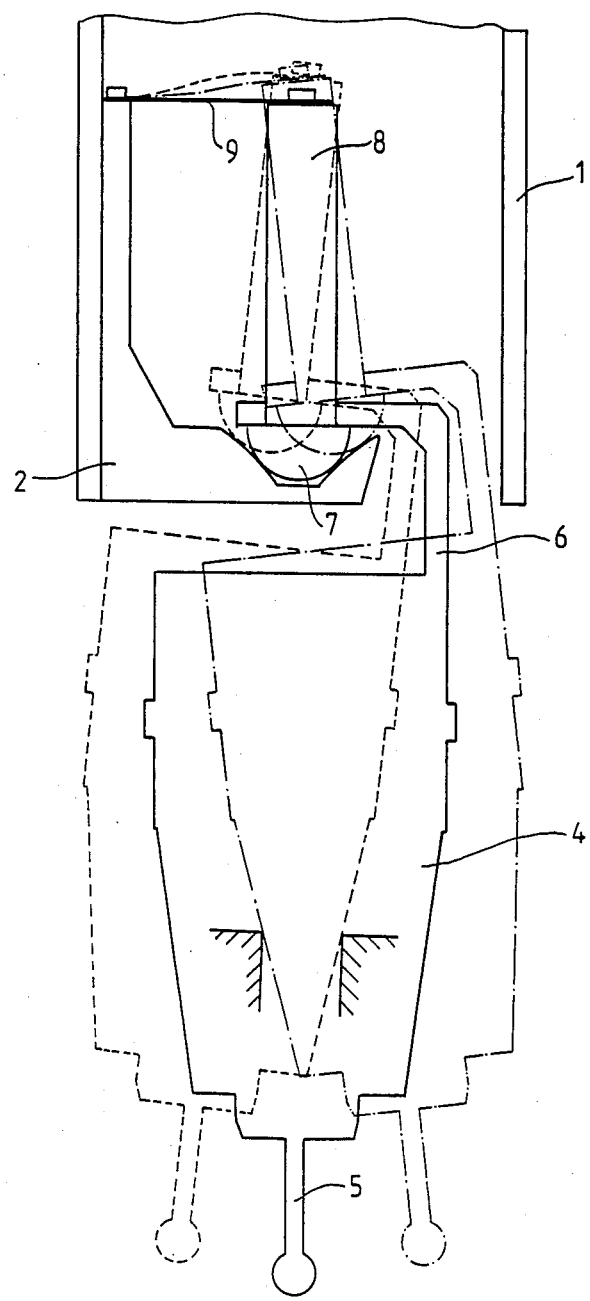
FIG. 3 is a schematic diagram explaining disengagement movement involved in operation of the invention.

However, the sensing head 4 can yield in the event of collision with a workpiece. In such case, as shown in FIG. 3, the hemisphere 7 disengages from the depression 3. A switch 10 mounted to the carrier part 6a has contacts which will be understood to be so connected to the emergency stop button as to stop the drive of the measurement machine. After eliminating the collision condition, ball 7 returns under the weight of the sensing head 4 into the conical depression 3 and restores the centered at-rest position of the sensing head 4 with a high degree of precision.

The yieldability of the sensing head is assured with respect to all directions in space ±z, ±y and +z which enter into consideration for a collision involving the arrangement of FIG. 1. Yieldability in the direction −z is unnecessary, since the transverse dimensions of the sensor head 4 do not exceed those of the spindle 1 from which it is suspended.

Figure 2:
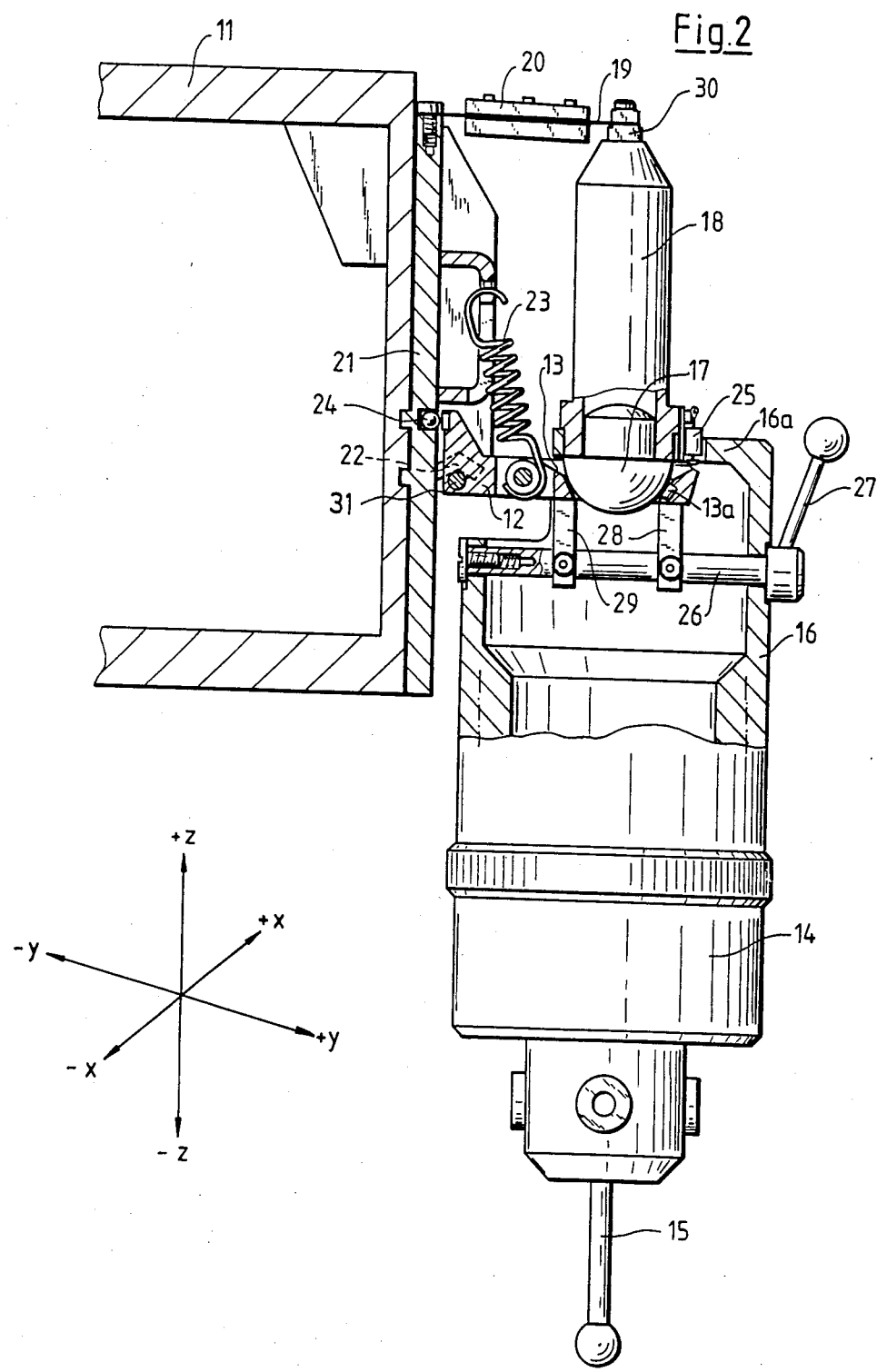
FIG. 2 is a view similar to FIG. 1, for a second embodiment.

In the embodiment of FIG. 2, a sensing head is mounted in collision-protected manner to the end of the horizontal arm 11 of a measuring machine of cantilever design. In this type of machine, yieldability of the sensing head 14 in the event of a collision is required in all six directions in space ±x, ±y and ±z.

In this embodiment, the upper end of a sensing head 14 is also secured to a carrier 16 having a hook-shaped part 16a which mounts a hemisphere 17 on its underside. The carrier 16 is suspended via this hemisphere 17, in a conically tapering depression 13. Also as in FIG. 1, an upstanding tubular rod or sleeve 18 is connected to the carrier part 16a, and, via an attachment part 30, a leaf spring 19 connects the upper end of sleeve 18 to a holding plate 21 mounted to the end of extension arm 11; leaf spring 19 thus secures the sensing head 14 against torsion about and tilting with respect to the z axis.

Yieldability in the −z direction is obtained by hinge-mounting the L-shaped part 12 which carries the centering concavity 13; specifically, the L-shaped part 12 is a rocker which can swing or rock about a horizontal pin 3. The pin 3 of part 12 locates in an inverted V-shaped yoke 22 on the holding plate 21, and part 12 is continuously urged by a tension spring 23 (acting between rocker 12 and holding plate 21), against an abutment ball 24 on the holding plate 21. The drive-disconnect switch 25 which is carried by part 16a responds not only upon dislocating displacement of the hemisphere 17 but also upon a yielding of the sensing head in the −z direction when the rocker 12 displaces about pin 3 (against the tension force of spring 23); even though ball 17 may remain seated in concavity 13 during a −z displacement, the switch 24 will nevertheless be sensitive to the −z displacement because switch 25 is at offset from ball 17 and is poised for response to the outer end of rocker 12.

The sensing head 14 can be locked in position manually by means of a hand crank 27, thus placing the anti-collision device out of operation. For this purpose, crank 27 actuates two eccentric cams 28 and 29 on a horizontal shaft 26, which is journaled in carrier 16 below rocker 12. Upon actuation of crank 27, cams 28 and 29 engage the bottom of rocker 12 and thus clamp the latter to the carrier 16. Since the axis of the shaft 26 is perpendicular to the axis of tilt 3 of the rocker 12, and in view of the stiffness of the leaf spring 19 in the y-direction, the clamp is also effective to lock against tilting movement of the rocker 12.

Figure 4:
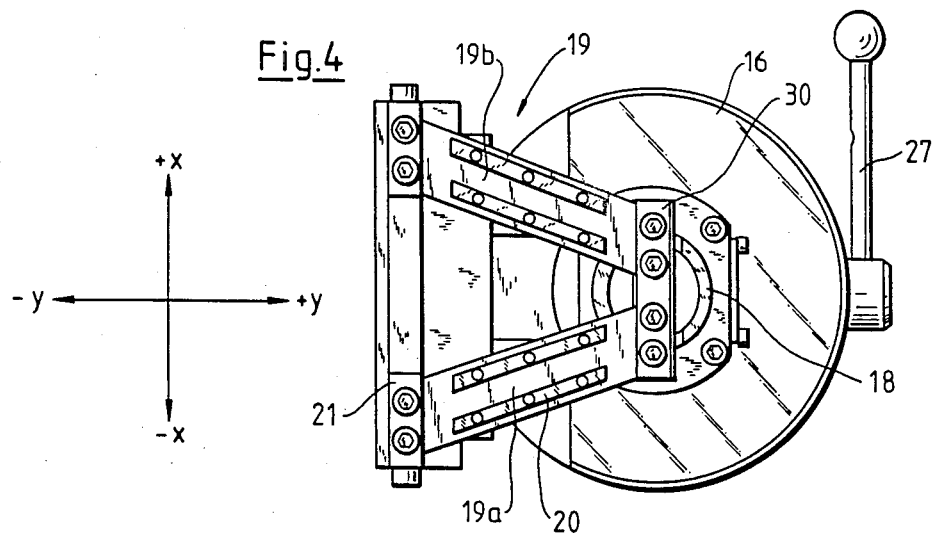
FIG. 4 is a plan view of the embodiment of FIG. 2.

The plan view of FIG. 4 clearly shows the leaf spring 19 which secures the sensing head 14 against torsion about the z axis. The leaf spring is formed of two strips of spring steel 19a and 19b arranged in a V pattern, and each strip is longitudinally stiffened by ribs 20. As a result of the division into two leaf springs, tilting about the y-axis of symmetry is readily possible, so that disengagement of the ball 17 from the depression 13 in the event of collision in the direction of the y-axis is assured. The V-shaped arrangement, on the other hand, prevents translation of the top of the rod 18 in the y-direction and thus secures the sensing head in centered position, i.e., with ball 17 engaged, against tilting.

Figure 6:
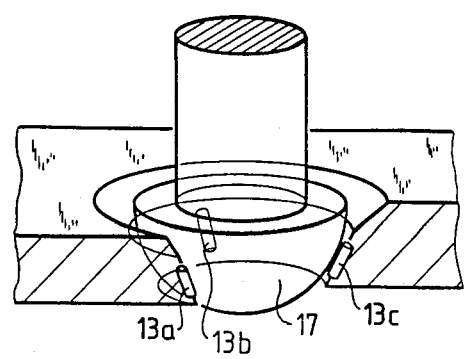
FIG. 6 is an enlarged view in perspective, partly broken-away and in section, to show detail of centering structure in FIG. 2.

From the perspective view of FIG. 6, it can be seen that three angularly spaced cylinders 13 (a-b-c) having their longitudinal axes inclined to the z axis and to each other are fixed in the conical concavity 13 in which the hemisphere 17 centers itself. Ball 17 therefore rests on three discrete points of contact, thus offering advantages of reproducibility of the at-rest position, as compared with ball seating in a purely conical concavity.

Figure 5:
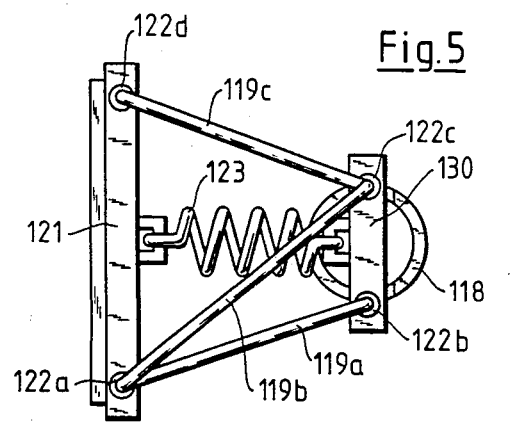
FIG. 5 is a plan view to show an alternative of FIG. 4 structure.

As an alternative to the leaf spring 19 in the embodiment of FIGS. 2 and 4, the anti-torsion element of FIG. 5 comprises three bars 119 (a-b-c) and a tension spring 123. The ends of the bars 119 (a-b-c) are mounted via self-aligning ball bearings 122 (a-b-c-d) respectively at two spaced points on the carrier plate 121 and at two spaced points on a fastening part 130 at the upper end of the vertical rod 118, the tension spring 123 assuring freedom of play. The N-shaped arrangement of the three bars 119 (a-b-c) also secures the top of the rod 118 against torsion about the z axis and against translation in the plane of the x and y axes, while also permitting rotation about the x and y axes, and displacement of part 118 in the z-direction.

What is claimed is:

1. An anti-collision probe suspension for a coordinate-measuring machine or the like, comprising a bracket adapted for connection to the machine in such manner as to establish a vertical arm connected to a horizontal arm, a probe head having a yieldable suspension connection to said bracket, said head having a central axis which is vertical in an at-rest connected condition of pendulous suspension from said horizontal arm, the suspension connection comprising coacting ball and socket elements which are self-centering on said axis and wherein the socket element provides a generally conical seat on which the ball element may ride in response to an off-axis displacement of said head, the suspension connection including means establishing anchorage against torsional displacement of said head about said axis while also yielding for other possible relative displacement of said head with respect to said support member.

2. The probe suspension of claim 1, in which said suspension connection includes an upstanding arm that is rigidly related to said probe head and which extends vertically above said ball and socket elements, said means establishing anchorage against torsional displacement being a flexible horizontally extending connection from said vertical arm to said upstanding arm.

3. The probe suspension of claim 1, in which said means establishing anchorage against torsional displacement is a leaf spring.

4. The probe suspension of claim 1, in which said bracket is characterized by a horizontal-axis pivotal connection of said vertical and horizontal arms with stop means limiting upward displacement of said horizontal arm and spring means biasing said horizontal arm to its stop-limited position, whereby in the presence of force exceeding the biasing force, said horizontal arm is downwardly deflectable.

5. The probe suspension of claim 4, further comprising selectively operable means for locking said ball and socket elements in their self-centered relation.

6. The probe suspension of claim 5, in which said selectively operable means comprises two eccentric cams on a shaft journalled in said probe head and poised to engage the underside of said horizontal arm at diametrically opposed offsets from said central axis, and an actuating handle for selective partial rotation of said shaft.

7. The probe suspension of claim 1, further comprising electric-switch means positioned to operate in response to dislocation of said ball and socket elements from their self-centered relation.

8. The probe suspension of claim 1, in which said ball element is a spherical segment and said socket element is a conical depression.

9. The probe suspension of claim 8, in which said conical depression is defined by three like cylindrical elements equally inclined to said central axis and at equal angular spacing about said central axis.

10. In a coordinate-measuring machine, a movable measuring-support member with a sensing head having a yieldable suspension connection to said member, said head having a central axis which is vertical in an at-rest condition of pendulous suspension for measurement, the suspension connection comprising coacting ball and socket elements which are self-centering on said axis and wherein the socket element provides a generally conical seat on which the ball element may ride in response to an off-axis displacement of said head, the suspension connection including means establishing anchorage against torsional displacement of said head about said axis while also yielding for other possible relative displacement of said head with respect to said support member.

* * * * *